United States Patent [19]
Wenner

[11] Patent Number: 5,141,521
[45] Date of Patent: Aug. 25, 1992

[54] HIP JOINT PROSTHESIS SHANK

[75] Inventor: Ulrich Wenner, Uelzen, Fed. Rep. of Germany

[73] Assignee: Man Technologie Aktiengesellschaft, Munich, Fed. Rep. of Germany

[21] Appl. No.: 521,152

[22] Filed: May 8, 1990

[30] Foreign Application Priority Data

May 17, 1989 [DE] Fed. Rep. of Germany ....... 3915983
Jun. 13, 1989 [DE] Fed. Rep. of Germany ....... 3919192
Jul. 28, 1989 [DE] Fed. Rep. of Germany ....... 3924990

[51] Int. Cl.$^5$ .............................................. A61F 2/36
[52] U.S. Cl. ...................... 623/23; 623/901; 623/22; 623/16
[58] Field of Search ...................... 623/23, 66, 901, 16, 623/18; 264/45.1, 45.3, 219, 222, 231; 249/160

[56] References Cited

U.S. PATENT DOCUMENTS

| | | | |
|---|---|---|---|
| 2,473,723 | 6/1949 | Nelson | 264/222 |
| 3,893,196 | 7/1975 | Hochman | 623/18 |
| 4,459,708 | 7/1984 | Buttazzoni | 128/92 |
| 4,750,905 | 6/1988 | Koeneman et al. | 623/16 |
| 4,978,360 | 12/1990 | Devanathan | 623/66 |

FOREIGN PATENT DOCUMENTS 9015708 12/1990 Fed. Rep. of Germany ........ 623/16

Primary Examiner—David Isabella
Assistant Examiner—G. Gualtieri
Attorney, Agent, or Firm—Ladas & Parry

[57] ABSTRACT

In the method for the production of a hip joint prosthesis shank two shells are produced with unidirectional fibers, which extend in the longitudinal direction of the shank and prior to curing of matrix material therein the components are assembled so that during the later curing stage there is an intimate engagement produced between the components. The fibers are wound on a shape, which has the desired form of the shell, by winding a single fiber lengthwise of the form and reversing the fiber at the ends of the form. The winding is carried out by pulling the fiber taut along the length of the form and reversing the fiber at the ends on pins and relatively turning the form and the fiber after completing the winding of the fiber over the length of the form. The core may be produced by introducing foaming or liquid material into the cavity formed by the shells.

20 Claims, 3 Drawing Sheets

HIP JOINT PROSTHESIS SHANK

BACKGROUND OF THE INVENTION

The invention relates to hip joint prosthesis shanks and to methods of their manufacture in the form of fiber-reinforced resin structures with an at least partial longitudinal alignment of the fibers.

The German patent publication 2,753,568 C3 describes a shank of this type in which the fibers extend in the longitudinal direction of the shank and in which only the fibers located on the surface extend from one end as far as the other end of the shank. The consequence of this is that forces which are applied to the upper, proximal end of the shank are only able to be transmitted by a part of the fibers to a curved part of the shank, more especially since the inner fibers of this shank end do not in part extend as far as this curved part.

SHORT SUMMARY OF THE INVENTION

One object of the present invention is to provide a prosthesis shank of the initially noted type in which there is an optimum transmission of the forces in the shank.

In order to achieve this or other objects appearing from the present specification, claims and drawings, the shank is made up of a core and a casing, the latter being composed of longitudinally directed fibers.

In this case a core with irregular geometry forms an inner displacing body around which the fibers, which are responsible for the stiffness of the shank, are laid without any interruption from one shank end as far as the other shank end so that the fibers are arranged in mutual parallelism in the longitudinal direction of the shank. As a result all the fibers ending at the upper end of the shank, which has the force imparted to it, take part in transmitting the forces into other parts of the shank so that there is an optimum utilization of the reinforcing properties of the fibers.

The transmission of the forces remains in the casing, that is to say in the superficial part of the shank and in the vicinity of the surrounding bone material in the implanted state. As a result the forces are transmitted via the fibers directly into the bone growth zone or any intermediate cementing material. There are no intermediate components, which might become detached due to applied loads.

At least at one end of the shank the fibers will occupy the full cross section, whereas in the rest of the shank they surround the core. In this respect it is important that the cross sectional area of the casing is the same at the end of the shank as in the core part, that is to say in cross section the casing has the same number of fibers along the full length of the shank.

The invention furthermore provides a method for producing such a shank in which using endless fibers at least two components of the shank are produced and are joined together to form the shank, such components being in the form of at least two shells which are produced separately with the fibers aligned in the longitudinal direction of the shank and the fibers thereof are impregnated with a matrix and furthermore a core is produced whose outer form corresponds to the cavity which is formed by assembly of the shells and the shells are placed around the core and all the parts of the shank are joined together.

In the method in German patent publication 2,753,568 the fibers are made into a ring, whose form in portions corresponds to parts of the form of the shank which is to be manufactured. After curing of the ring these sections are removed from the ring and bonded together to form the shank. Although this method does make it possible to manufacture the geometrically irregular shank with continuous longitudinal fibers at least on the surface, in the case of a shank with an approximately round cross section the method involves substantial difficulties and for the further fibers the method is not possible.

In the method in accordance with the invention on the other hand the production of two or more shells extending along the length of the shank makes possible to cause all fibers occurring at one end to extend as far as the other end of the shank.

In the case of two shells the longitudinal section of the shank is such that its section surface extends perpendicularly to the plane in which the curvature of the shank is contained. This means that there are two components, which have a curvature or curved part able to be wound, that is to say the curvature of the shank. The longitudinal direction of the shells thus corresponds to the longitudinal direction of the shank. The longitudinally direction fibers are bundled in the two shank parts, whereas in the middle part they are fanned out and form the shell-like structure. When the shells are joined together, the result is a hollow body, whose wall is formed by unidirectional fibers extending parallel to the wall. The result is the possibility of an optimum transmission of forces from the upper end of a shank to the widened out middle part. Radial forces are opposed by the core filling the cavity without leaving any gaps.

The shank produced in accordance with the invention is compact and its outer form may be adapted exactly to the optimum configurations. More particularly conical end parts may be produced with true shaping and with continuous fibers.

In accordance with a further embodiment of the invention the shells and the core are produced as prepreg components, that is to say without precuring and it is only after assembly and heating that they are fully cured. This procedure involves the advantage that the fiber matrix structure is continued homogeneously at the joints so that there are no adhesive bonds or discontinuities in the structure of the shank. The shells responsible for the stiffness of the shank thus together form a homogeneous member.

For the curing operation the components are preferably placed in a mold and kept under pressure during curing. The sectional surface of the mold is preferably perpendicular to the sectional surface of the shells. Preferably, low pressure is used which is just sufficient to produce a satisfactory contact over a wide area between the components. This ensures that no matrix material is squeezed out.

It is obviously possible to make the fibers not of two half shells but of three of more shells if this should be desirable for reasons of manufacturing technology and owing to the shape of the shank, more particularly as regards winding the shells. Generally two shell parts, that is to say half shells, are preferred, more particularly if in order to provide for different shank sizes different winding devices have to be provided.

For the shaping of one shell it is preferred to use a negative mold which, dependent on the form or outline of the shell, has a convex or a concave surface, on or in which the impregnated fibers are wound in the longitudinal direction or are laid therein with the fibers under tension. In the length direction of these shells (which corresponds to the length direction of the finished shank) the negative mold is in each case convex, this being a sine qua non for winding in such a case. The transverse direction thereto may, on the other hand, be convex or concave. In order to overcome these positions supporting molds are used, which prevent the fibers sliding out of place. At the ends of the negative mold, respective auxiliary pins are provided around which the fibers are trained for the return winding stroke. In this manner a mechanical winding method is made possible, in which the fibers are trained backwards and forwards in a reciprocating motion and trained about the pins.

The ends of the shank are generally made solid, that is to say made up of the bundled unidirectional fibers without any central cavity, more especially if the shank ends have the same cross section. In the intermediate zone the fibers are fanned out and form a shell shape in one or more layers resting alongside each other. In this manner all the fibers will extend from one shank end to the other with a homogeneous distribution on the periphery of the cylindrical shell part. This part is located approximately at the bend in the shank where there is transmission of forces from the fibers to the surrounding femur bone wall. If in this case different loading effects have to be taken into account, the fiber distribution may be nonhomogeneous to a suitable degree in the shell zone. In the method in accordance with the invention it is possible to form conical shanks in which all fibers run through the cone from the small to the large cross section. In the larger cross sectional area a cavity will be left, which is able to be subsequently filled with the core.

In the case of different cross sectional areas at the shank ends it is possible for the number of fibers to be set to take into account the cross section of the thinner shank end. Then a certain cavity will be produced at the other end of the shank. The thinner shank end will as a rule be the lower one which is implanted into the femur. In this case it may also be expedient for the number of fibers to be set in accordance with the cross section of the upper shank end in such a manner that this end is compactly filled with fibers. In this case the lower end has to be made thinner by a mechanical operation.

The materials used in the invention may be those conventionally used for the manufacture of prostheses, such material being preferably carbon fibers with a conventional biocompatible matrix material in order to optimize rigidity.

Endless fiber material may be used for the shells, which in the finished state of the shank runs parallel to the outer face of the shank in the longitudinal direction so as to ensure optimum stress loading of the shell. The filling member may be produced using any suitable fiber composite manufacturing method. Since the filling body does not have to withstand any exceptional loads apart from radial thrusts, the core is preferably made by pressing using short fibers. For this purpose it is preferred to use the same materials as for the shells.

The filling body may be utilized to accommodate medicinal devices or instruments and for medicaments or the like for influencing the body of the implant wearer with the purpose of checking the performance of the prosthesis and to check measures for medicating the user after implantation.

In accordance with a further development of the invention the core is not in the form of a solid prefabricated structure but is in the form of a liquid, which may be viscous or adapted to be foamed, which is introduced into the cavity, that is formed when the prefabricated shells are assembled with each other.

The geometrically irregular outline or surface of a shank means that the assembled shells, which constitute the casing, also define a geometrically irregular cavity.

Owing to the introduction of a material in a liquid or foaming state into the cavity it is possible to completely fill the cavity using a very simple production technique. This means that the production technology for the method is optimized, since there is no need to produce a prefabricated core with a precise configuration and there is a complete and a continuous bond between the core and the shells.

Since the number of fibers remains constant for all cross sections of the shank, there will as a rule be a channel at one end of the shank connected with the internal cavity. This channel is employed in order to introduce the material for the core after the assembly of the shells. It is naturally possible to provide one or more orifices at some other convenient point for the introduction of the core material.

The material for the core may include admixed short fibers for imparting strength to resist radial forces, a contrast agent for medical purposes or other substances.

The shells for the casing are held, preferably in a mold, in the assembled state. For this case it is expedient for the material for the core to be introduced under a low pressure in order to lightly press the shells against the inner face of the mold and thus to achieve optimum alignment of the fibers. In order to oppose a tendency to shrink during curing the material for the core is introduced with a suitably increased pressure. Furthermore in many applications it is appropriate to clad the cavity wall with a foil or film.

The invention will now be described in more detail with reference to working examples thereof as diagrammatically shown in the drawing.

DETAILED DESCRIPTION OF WORKING EMBODIMENTS OF THE INVENTION

Figure 1:
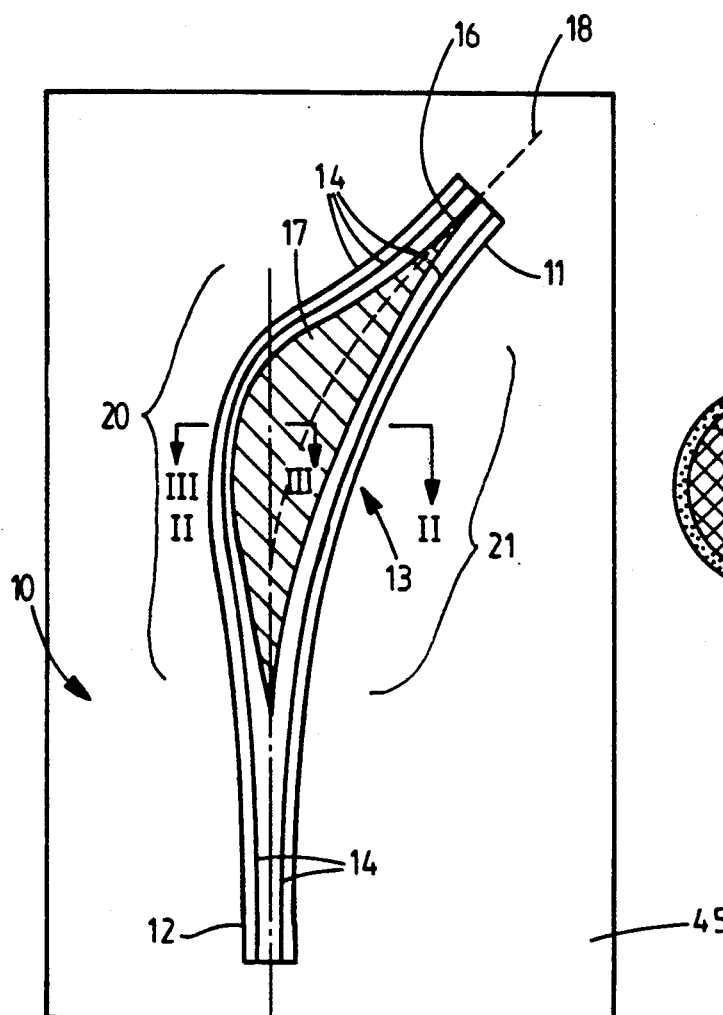
FIG. 1 is a longitudinal section of the shank of a hip joint prosthesis.

FIG. 1 shows a longitudinal section of the shank 10 of a hip joint prosthesis, the shank having an approximately cylindrical proximal upper end 11 to receive a prosthesis condyle (not shown), a lower or distal end 12 and a bent middle part 13 which has a larger cross section. The lower end 12 is entirely made of longitudinally orientated fibers 14, which extend past the middle part 13 to the upper end. Owing to the increase in cross section in the middle part 13 and the larger cross section of the upper end the fibers 14 in the middle part form an outer skin 15, whereas at the upper end 11 they leave a narrow channel 16. The cavity between the fibers 14 is completely filled by a core 17, which is able to take up radial forces.

Figure 2:
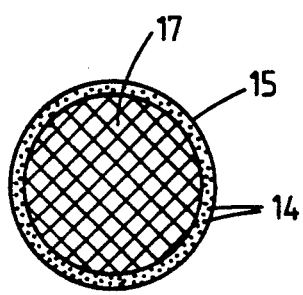
FIG. 2 is a transverse section through the shank along line II—II in FIG. 1.

FIG. 2 shows a cross section taken through the middle part 13 to indicate the outer skin 15 made of fibers and which surrounds the core 17.

The fibers 14 forming the shank ends 11 and 12 and the outer skin 15 completely encase the core 17, which only has a displacing or filling function. The mechanical properties of the shank 10 are essentially determined by the longitudinally directed fibers 14, whose number remains constant along the entire cross section of the shank 10. The result of this is that the cross sectional areas, both of the outer skin 15 and also of the shank ends 11 and 12, are all equal. This leads to an optimum transmission of forces from the upper shank end 11 into the shank 10 and to the surrounding bone material.

In order to produce a shank as shown in FIG. 1, the first step is to produce components of the structure made up of the parts 11, 12 and 13 having the longitudinal fibers 14, the components being shell-like structures separated by longitudinal interfaces and which will be referred to as shells. In the simplest case the shell is made up of two shell halves, whose joint interface conforms to a longitudinal section of the shank 10, whose section surface or area extends perpendicularly to the bend or flexure surface, that is to say perpendicular to the plane of FIG. 1.

Figures 3, 4:
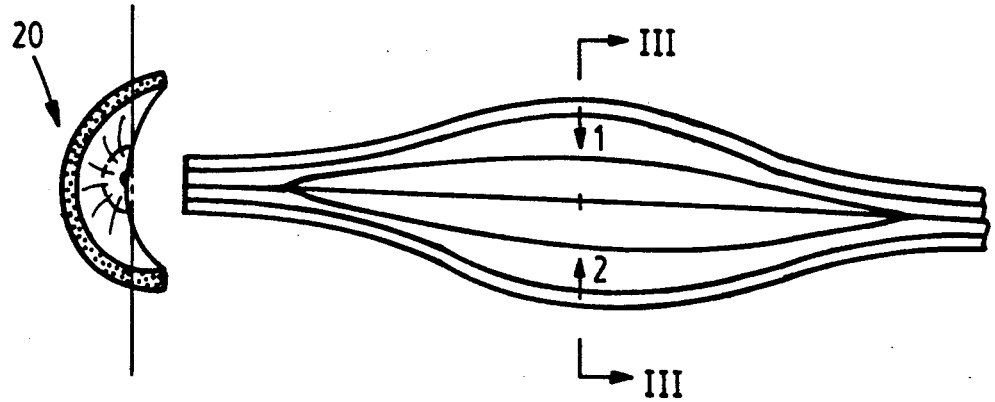
FIG. 3 is a transverse section of a component of the shank taken along line III—III in FIG. 1.
FIG. 4 is an elevation view of the shank.
Figure 5:
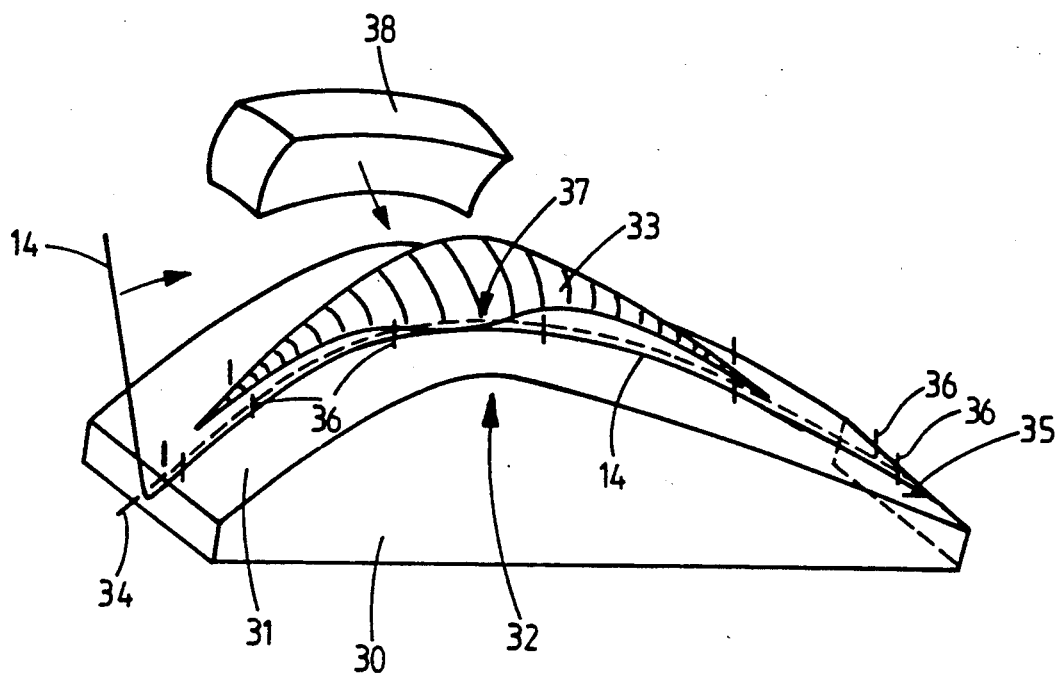
FIG. 5 shows one mold for the production of the components of the shank.
Figure 6:
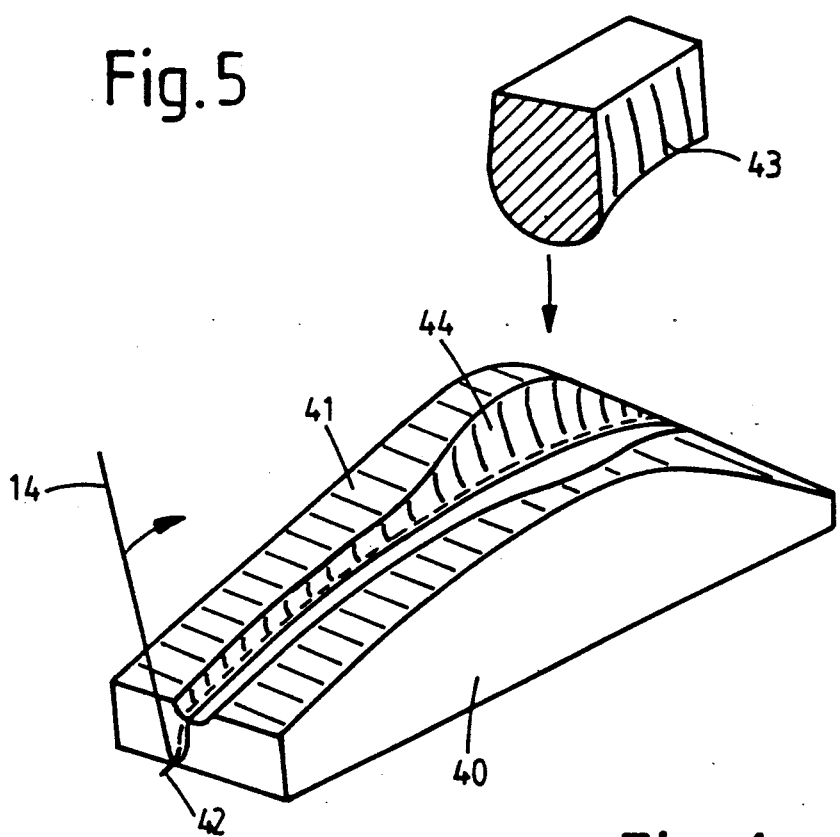
FIG. 6 is a view of a further mold for this purpose.

FIG. 3 is a section taken on the line III—III of FIG. 1, to show a shell half 20 whose section is the left hand half of FIG. 1. FIG. 4 is an internal view of this first shell half. To wind the first shell half 20, which defines the convex surface or curvature of the shank 10, a mold 30 as shown in FIG. 5 is utilized, whose winding surface 31 defines the curved surface 32 of the shank 10. On the winding surface 31 the mold 30 has a protrusion 33, which corresponds to the outer surface of the one half of the middle part 13 when the thickness of the wall of the shell 15 is taken into account. The winding operation is performed by guiding the running fiber 14 to and fro so that it is deflected at the ends of the mold 30 about respective pins 34 and 35. The fiber 14, which is drawn through an impregnating device for applying matrix material thereto, is in the example of FIG. 5 fixed on the right hand end and drawn or laid over the winding surface 31. In order to guide the first fiber 14, auxiliary pins 36 are provided in order to prevent lateral slipping of the fibers 14 out of position.

Upon reaching the left hand end the fiber is deflected about the bend pin 34, as shown in broken lines, and drawn across to the right hand end. When this is done in the starting part the fiber comes to rest alongside the first thread and in the protrusion part 37 on the first thread. In the case of a mechanical winding process the mold 30 is oscillated as the fiber 14 is trained to and fro. In order to prevent any slipping out of position of the superposed fibers 14 in the protrusion part 37 a displacing or filling mold 38 or jig is used, which is placed on the protrusion 33 so as to leave a gap.

In the drawing, the filling or displacing mold 38 is shown for the sake of simplicity at the side which is to the rear of the protrusion. During winding another suitable displacing mold (not shown) is placed at the front at the protrusion. When the fiber 14 reaches the upper meridian, the winding process is continued from the rear lower side so that the fibers come into a superposed relationship in the protrusion part 37 owing to the effect of the displacing mold 38. The sequence and the direction of winding are indicated in FIG. 4 by the arrows 1 and 2.

The second shell half 21 is wound in a similar manner using a mold 40, whose convex winding surface 41 is this time not provided with a protrusion but with a recess or depression 44. In this case as well bend or deflection pins 42 are used around which the fiber 14 is trained in a reciprocating manner with an alignment in the longitudinal direction, but here it is not wound from the edge but from the middle, that is to say from the deepest position so that in this instance too one fiber is able to be superposed on the last fiber wound owing to the provision of the displacing mold 43. After one half of the second shell half has been wound, the operation is recommenced from the bottom.

It is important for the fiber 14 to be positioned in a suitably taut condition on or in the mold 30 and 40 so that there is the advantage of a winding method for the mechanical strength of a mold body.

In the method in accordance with the invention the number of fibers is the same in every cross section of the shank 10. The appropriate number of fibers is calculated on the basis of the thickness of the fiber and the thinnest cross section of the shank. Thus, one shank end (as for instance the shank end 12, FIG. 1) will be entirely filled with identically orientated fibers 14, whereas the other somewhat thicker shank end 11 will form a corresponding central cavity, when the two shells 20 and 21 are put together. In the middle part 13 the fibers are homogeneously distributed over the outer skin 15. It is thus possible to cope with the transmission of a force which is irregularly distributed over the circumference of the shank by having more fibers in the zone in question. If for instance in FIG. 1 the right hand side in the middle part 13 has to be made more rigid, the interface 18 between the shells 20 and 21 will be so displaced out of the central position that there will be more fibers present in the right hand shell 21 than in the left hand shell 20.

It will thus be seen that the method in accordance with the invention is a highly adaptable one making it possible for both the mechanical strength and also the outline and general configuration of the shank to be so exactly selected as may be necessary for optimum use of the shank. The precise shaping of the shank may be attained in a simple manner by suitable design of the winding molds 30 and 40. In this respect it is also possible to form conical shank ends 11 or 12 of equal strength.

The core 17 is a compacted body, whose outline precisely corresponds to the shape of the cavity which is formed when the shells 20 and 21 are put together. The filling body may be produced by using conventional methods and may consist of any desired material. It may be produced as a fiber-reinforced composite material. In the case of a fiber-reinforced composite body it is preferred to use short fibers and for the core 17 to be conventionally compressed. In order to avoid any stresses or other interfering effects, the core is made of the same material or indeed of a material of the same type as used for the shells 20 and 21. If for instance carbon fibers are used for the shells 20 and 21 it is possible for carbon fibers or pitch fibers to be used for the core 17. For the matrix it is necessary to employ a biocompatible material. Such materials are described in the literature.

The core may also be made hollow and may be filled with contrast agents, medicaments and other materials relevant for the treatment of the user of the prosthesis.

After being produced in the method as described above the components 17, 20 and 21 are removed from the mold in an uncured condition, in assembled state to form the shank 10 and placed in a compression mold 45.

The compression or pressure mold consists of two mold halves, which have the same shape as the shank 10 but are slightly oversize. The interface between the two halves of the mold extends perpendicularly to the section surface 18 or area thought of as being ideal for the production of the shells. In FIG. 1 one mold half of the pressure mold 45 is shown. After placing the suitably assembled components 17, 20 and 21 in the compression mold 45, the two mold halves are pressed together until the mold surfaces engage, the as yet uncured shank 10 being kept under a suitable pressure. It is in this manner that the shank 10 or, respectively, the components 17, 20 and 21 are fully cured at a suitable temperature. Owing to the suitably adapted shape and the pressure exerted by the pressure mold 45 the surfaces of the components 17, 20 and 21 are so contacted that they more or less coalesce without leaving any traces of joints.

Figure 7:
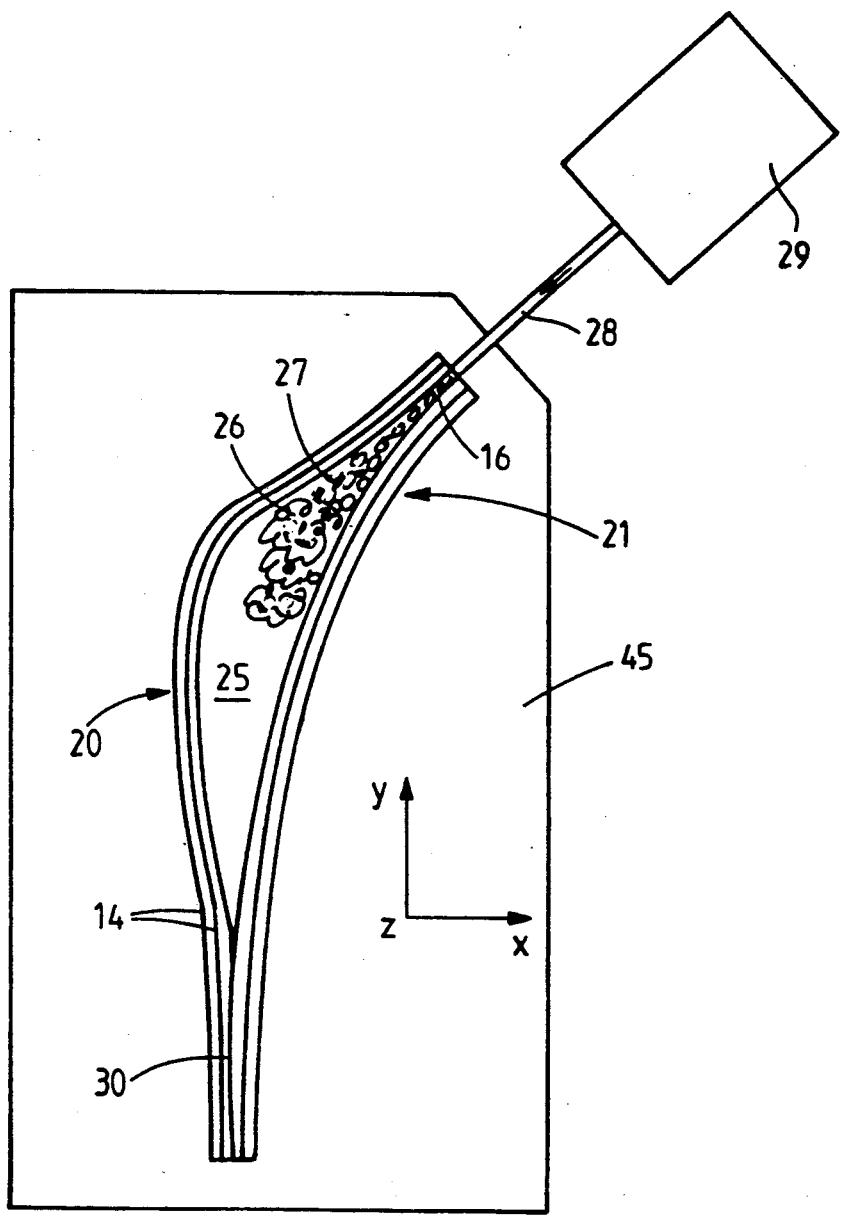
FIG. 7 is an elevation view of a further working embodiment of the invention.

FIG. 7 shows an example in which after the production of the shells the latter are placed in an uncured state in the mold which is able to be assembled, and of which one half 45 is depicted in the drawing. The contact interface with the second mold half in an XY plane, while the contact area or face or the interface 18 between the shell halves 20 and 21 is perpendicular to the XY plane. The shells 20 and 21 are kept together in the two mold halves 45, of which only one is shown in FIG. 7, and owing to their configuration they form the cavity 25, which may be accessed from the outside via the channel 16 in the upper end of the shank. Material 26 is supplied via a duct 28 from a reservoir through the channel 16 into the cavity 25. The material 26 may be a composition adapted to foam or a liquid resin with or without additives. When introducing the material 26 for the core 17 it is important that the material fill the cavity 25 as fully as possible. The method to be employed will depend on the viscosity and the other properties of the material 26. Thus, it is, for example, possible to inject a foamable composition directly from a collapsible tube into the cavity 25. As a rule, however, a pressure pipe 28 is employed via which the material is able to be injected under pressure. In this respect steps have to be taken to provide for adequate evacuation of the cavity 25. In place of the channel 16 it is, however, possible for the material to be introduced through any other orifice in the middle or other part of the shank.

If desired short fibers 27 and also contrast agent and the like may be mixed with the material 26.

After the charging of the cavity 25 with a suitable material 26 the curing of the resin in the shank within the molds 45 is caused to take place, the matrix of the shells 20 and 21 producing a seamless connection at the joints 30. In a similar manner an intimate connection is produced between the matrix of the shells 20 and 21 and the material 26. Pressure may be developed using within the cavity 25 in order to oppose any tendency to shrink. A lining on the inner wall surface of the shells 20 and 21 may be employed to ensure that local excess pressure does not impair the fiber structure of the shells at certain points.

What is claimed is:

1. A hip joint prosthesis shank comprising an elongated member including an upper end portion, a lower end portion and a middle portion having a bend therein, said middle portion having a larger cross-sectional area than cross-sectional areas of said upper and lower end portions, said elongated member including an outer casing and inner core, said casing entirely surrounding said core, said core having a variable cross-sectional area along the length of the elongated member and said cross-sectional area being a maximum in the region of said bend in the middle portion, said casing comprising a plurality of fiber elements extending longitudinally of said elongated member over the length thereof and occupying a constant area in the cross-section of the elongated member over substantially the entire length thereof.

2. A shank as claimed in claim 1 wherein said outer casing comprises a matrix in which said fiber elements are embedded.

3. A shank as claimed in claim 2 wherein said casing comprises a plurality of shells cooperatively and integrally engaged to surround said core.

4. A shank as claimed in claim 3, wherein said shells are half shells, said half shells having longitudinal faces along which said half shells are joined.

5. A shank as claimed in claim 2 wherein a number of said fiber elements are formed by a single fiber which is wound back and forth lengthwise of the elongated member and undergoes reversal at the ends of the elongated member.

6. A shank as claimed in claim 5 wherein said casing defines an interior cavity containing a filling material to constitute said core.

7. A shank as claimed in claim 1 wherein the number of fiber elements in the casing is equal over the length of the elongated member.

8. A shank as claimed in claim 2 wherein at said lower end portion said casing constitutes substantially the entire cross-section of the elongated member.

9. A shank as claimed in claim 2 wherein said fibers are in tension state in said casing.

10. A method of producing a hip joint prosthesis shank comprising
    forming an elongated member having upper and lower end portions and a middle portion with a bend therein of larger cross-sectional area than cross-sectional areas of the upper and lower end portions,
    forming the elongated member with an outer casing entirely surrounding a core,
    forming said outer casing by longitudinally winding a fiber back and forth in alternating opposite directions on a form with reversal of the direction of winding of the fiber at the ends of the form so that the fiber provides adjacent lengths thereof which are wound in alternating opposite directions and the number of lengths of fiber are equal over the entire length of the form, and
    forming said outer casing as an integral body in which said lengths of fiber are embedded.

11. A method as claimed in claim 10 comprising embedding said lengths of fiber in a matrix in said integral body.

12. A method as claimed in claim 11 comprising forming said outer casing as a plurality of shell members and joining said shell members to form said casing.

13. A method as claimed in claim 12 comprising winding said fiber lengths in proximity to one another in said end portions and fanning said fiber lengths out in said middle portion.

14. A method as claimed in claim 12 comprising curing said matrix after the fibers have been embedded therein.

15. A method as claimed in claim 12 comprising effecting said winding after impregnating the fiber with said matrix.

16. A method as claimed in claim 12 comprising maintaining tension in said fiber after said winding.

17. A method as claimed in claim 12 comprising placing said shell members in a mold and effecting the joining of said shell member (2) under pressure.

18. A method as claimed in claim 12 comprising effecting relative turning between said fiber and said form as the direction of winding of the fiber is reversed.

19. A method as claimed in claim 12 wherein upon joining said shell members a cavity is formed therewith constituting said core, and comprising filling said cavity with a curable material, and curing said material.

20. A method as claimed in claim 19 comprising introducing said material into said cavity under pressure.

* * * * *

UNITED STATES PATENT AND TRADEMARK OFFICE
CERTIFICATE OF CORRECTION

PATENT NO. : 5,141,521
DATED : August 25, 1992
INVENTOR(S) : Ulrich WENNER It is certified that error appears in the above-identified patent and that said Letters Patent is hereby corrected as shown below:

On title page, item [73] Assignee:
change

"Man Technologie Aktiengesellschaft, Munich" to

"MAN Technologie Aktiengesellschaft, Munich"

Signed and Sealed this

Fourteenth Day of September, 1993

Attest:

BRUCE LEHMAN

*Attesting Officer*     *Commissioner of Patents and Trademarks*